United States Patent [19]
Yanai et al.

[11] Patent Number: 5,782,815
[45] Date of Patent: Jul. 21, 1998

[54] GLASS CARTRIDGE FOR INJECTION SYRINGE PREFILLED WITH PHARMACEUTICAL LIQUID

[75] Inventors: Yuji Yanai, Tokyo; Mitsuru Kakimi, Nishinomiya, both of Japan

[73] Assignees: Yuji Yanai, Tokyo; Nihon Schering K.K., Osaka, both of Japan

[21] Appl. No.: 590,479

[22] Filed: Jan. 24, 1996

[30] Foreign Application Priority Data

Jan. 26, 1995 [JP] Japan .................. 7-030003

[51] Int. Cl.$^6$ .................................. A61M 5/315
[52] U.S. Cl. ................ 604/218; 604/227; 604/240; 222/386
[58] Field of Search ................ 604/181, 187, 604/195, 199, 218, 220, 221, 222, 225, 232, 240, 241, 242, 243, 905, 283, 227; 215/317, 320, 324, 326, 329, 335, 337, 340, 341, 343, 344, 350, 352, 349, DIG. 3; 222/386

[56] References Cited

U.S. PATENT DOCUMENTS

| | | | |
|---|---|---|---|
| 2,517,689 | 8/1950 | Lement | 604/243 |
| 2,828,742 | 4/1958 | Ashkenaz | 604/242 |
| 3,511,239 | 5/1970 | Tuschhoff | 604/242 |
| 3,941,128 | 3/1976 | Baldwin . | |
| 3,978,858 | 9/1976 | Tischlinger | 604/227 |
| 3,987,940 | 10/1976 | Tischlinger | 604/227 |
| 3,989,044 | 11/1976 | Meierhoefer | 604/243 |
| 4,051,851 | 10/1977 | Tischlinger | 604/227 |
| 4,068,661 | 1/1978 | Hennings | 604/227 |
| 4,072,149 | 2/1978 | Tischlinger | 604/227 |
| 4,693,710 | 9/1987 | McCool . | |
| 4,747,839 | 5/1988 | Tarello et al. | 604/240 |
| 4,870,034 | 9/1989 | Keifer . | |
| 4,883,471 | 11/1989 | Braginetz et al. . | |
| 4,909,788 | 3/1990 | Egolf | 604/227 |
| 5,282,792 | 2/1994 | Imbert | 604/187 |
| 5,338,309 | 8/1994 | Imbert | 604/227 |
| 5,383,864 | 1/1995 | van den Heuvel | 604/232 |
| 5,403,288 | 4/1995 | Stanners | 604/241 |
| 5,487,737 | 1/1996 | Meyer . | |
| 5,554,133 | 9/1996 | Haffner et al. | 604/227 |

FOREIGN PATENT DOCUMENTS

| | | |
|---|---|---|
| 0 278 015 | 8/1988 | European Pat. Off. . |
| 0 327 519 | 8/1989 | European Pat. Off. . |
| 0902925 | 9/1945 | France ............ 604/241 |
| 90/07318 | 7/1990 | WIPO . |

*Primary Examiner*—Ronald K. Stright, Jr.
*Attorney, Agent, or Firm*—Wenderoth, Lind & Ponack, L.L.P.

[57] ABSTRACT

A glass cartridge (C) for an injection syringe prefilled with pharmaceutical liquid, wherein a glass barrel (1a) having an entrance end (1i) portion and the exit end (1e) portion are formed. Further, a stopper serving also as a piston is fitted into the glass barrel (1a), and a gasket (3) is provided on the exit end (1e). A lure lock lid (4) and a lid holder (5) are provided on the exit and (1e). An inner member (41) of the lure lock lid (4) is preferably made of polypropylene, PP while its outer member (42) is preferably made of polybutylene terephthalate, PBT. The lid holder (5) and a flanged cap (6) are preferably made of polycarbonate, PC, and the stopper (2) and the gasket (3) are made of isobutylene-isoprene copolymer rubber, IIR. Even when the glass cartridge for an injection syringe is prefilled with pharmaceutical liquid and subjected to pressurized steam sterilization (121° C.×20 min), alkaline metallic ions will be eluted.

21 Claims, 2 Drawing Sheets

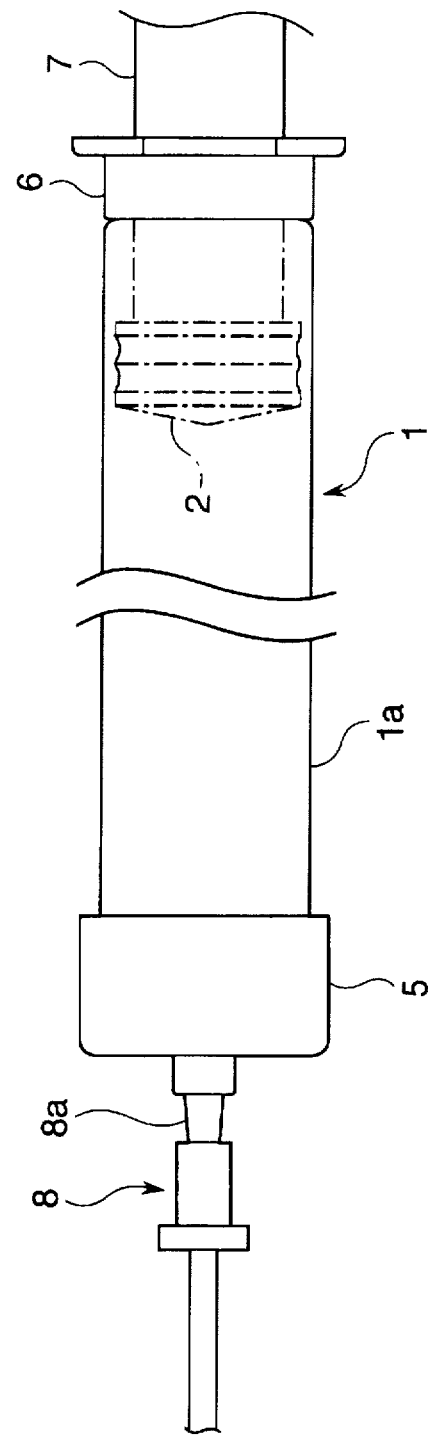
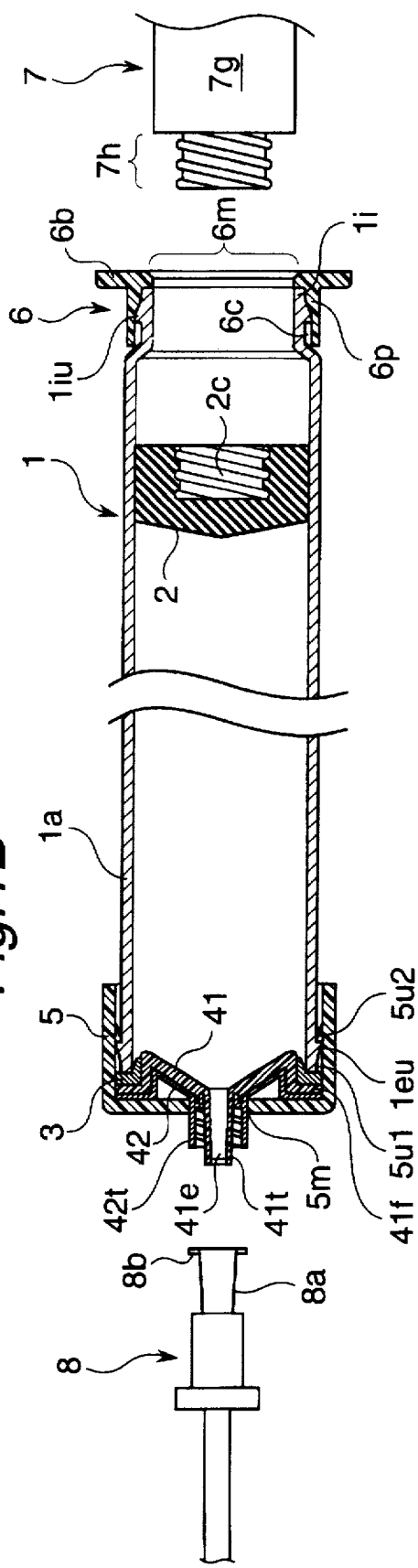

GLASS CARTRIDGE FOR INJECTION SYRINGE PREFILLED WITH PHARMACEUTICAL LIQUID

FIELD OF THE INVENTION

The present invention relates to a glass cartridge applicable to an injection syringe having a capacity of 50 to 300 ml prefilled with pharmaceutical liquid. In particular, the invention relates to a glass cartridge for an injection syringe capable of being prefilled with pharmaceutical liquid. The glass cartridge comprises a barrel made of a heat-resistant glass tube such as a boro-silicate glass. The barrel is closed by a lid provided on the exit end portion thereof. A tightly closed space, defined by a stopper serving also as a piston which when positioned on the area of the inner part entrance thereof, is filled with pharmaceutical liquid. Also a flange suited to a mechanism for loading it onto injecting device is provided on the entrance end portion.

BACKGROUND OF THE INVENTION

Currently, injection syringes are not supplied in the form that they are prefilled therein with pharmaceutical liquid, when they are the ones having relatively large capacities of 50 to 300 ml. Thus, under such circumstances, the system is always used, wherein after pharmaceutical liquid to be used is sucked into an empty syringe or an injection syringe (hereinafter called "an injection syringe") from a vial filled therewith via an injection needle, they are injected into a living body, such as a human body or the like.

The problem of this system lies in the fact that medical operators must do preparation work manually for replacing pharmaceutical liquid in the vial, and in particular it is necessary to repeat this work with the injection syringes having large capacities of 300 ml a number of times.

Also, a commonly used injection syringe made of plastic, such as a polypropylene etc., tends to become deformed due to a lack of its resistance and a rapid increase of an inner pressure when it is sterilized with steam water after filled with liquid chemicals. Moreover, since a gas barrier characteristic of such a plastic syringe is poor, it has been impossible to use this type of the injection syringe for pharmaceutical liquid requiring a high level of a gas barrier characteristic. The plastic injection syringe also has a problem that, in order to prevent deformation when carrying out sterilization with steam water, it requires a special technique such as applying heating under increased pressure or cooling under decreased pressure.

In addition, a strong sliding resistance is gradually given to a rubber piston in the injection syringe made only of plastics, such as a polypropylene, etc., with the incursion of the rubber piston caused by a taper for withdrawal (smaller at end) of the syringe. The taper is almost unavoidably given to the inner wall of the plastic injection syringe. Thus, in the case where cartridges made of resins having capacities of 50 to 300 ml, the cartridges are practically impossible to be used as the sliding resistance reaches an unusual strength.

As it is known, for the object of preventing manual handling of the syringe or the injection syringe, an injection syringe made of glass having capacities of below 20 ml has been produced, which comprises a barrel, an end wall sealing the exit end of the barrel and a liquid supplying hole provided for penetrating the end wall. However, in the case of glass cartridges having capacities of 50 to 300 ml, residual stress caused by strong heat applied for sealing or contracting the exit end tended to remain. The residual stress usually generated cracks on the exit end during transportation or storage. Further, such thermal stress also remained on a glass flange formed on the entrance end of the injection syringe, as well.

In the case where large capacity glass cartridges are produced from large diameter glass tubes, a sufficient annealing operation must be carried out so as to prevent cracks from generating after formation and it leads to a steep reduction in productivity.

Further, as for large capacity injection syringes both and of which are integrally processed from a large diameter glass tube directly, even when they are formed of neutral boro-silicate glasses, phase splitting is generated on glass components due to strong heat applied to both ends. Consequently, during the process where liquid chemicals are poured into a formed injection syringe and sterilization by pressure steaming (for example, 121° C.×20 min) is performed in an autoclave, or during a long period of storage time thereafter, alkaline metal ions(Na+,K+,Ca++,B3+, etc.) from the inner surface of the glass barrel wall are eluted in pharmaceutical liquid, such pH of the pharmaceutical liquid shifts to an alkaline side on the average by 1 (See Table 1 as described later).

As a result, pharmaceutical liquid, which is easily affected by a change of pH, usually degrades in various ways. In a conventional system, as a means to prevent such degradation, a process for neutralizing alkali metal ions by a so-called "sulfur treatment", (treating with dil. $H_2SO_4$ solution) etc., has been required.

OBJECT OF THE INVENTION

The present invention was made in order to provide a glass injection syringe which can be produced without causing residual stress on both ends of the glass tube body part. More specifically, the object of the present invention is to develop an injection syringe in which it is easy to seal the exit end, attach an injection needle, etc., and attaching a syringe flange to the loading mechanism of an injection device at the entrance end, which can be produced, without an integral shaping operation which tends to cause residual stress and thus leads to a gross drop in productivity when such residual stress is eliminated.

SUMMARY OF THE INVENTION

The inventors intensely worked to solve the problems associated with the prior art and have found that cartridges to be used for the injection syringes having relatively large capacities of 50 to 300 ml can be manufactured by using a glass tube without the integral shaping.

That is, when only a barrel of a pharmaceutical liquid cartridge is formed of a glass tube such as a boro-silicate glass tube, the following effect is achieved:

- High-level heat resistance and a gas barrier characteristic were realized; and
- Prevention of alkalization of the inner surface generated due to phase splitting of the glass components and "sulfur treatment", etc., considered to be an essential post process can be made unnecessary.

A glass cartridge for an injection syringe prefilled with pharmaceutical liquid according to the present invention comprises a barrel of a heat resistant glass provided with an undercut on an outer surface of the exit end portion and another undercut on an outer surface of the entrance end portion reducing the diameter of the glass barrel. A lid holder made of a flexible material is disposed on the exit end portion of the glass barrel so as to be engaged with the undercut. A gasket made of a soft material is provided and is disposed between the lid holder and the exit end of the glass barrel. A lure lock lid made of a flexible material is provided between the gasket and the lid holder. A stopper serving also as a piston is disposed in the glass barrel, and a flanged cap made of a flexible material is provided on the entrance end portion of the glass barrel engaged with the undercut.

In the glass cartridge for the injection syringe of the present invention the glass barrel may be a linear transparent glass tube formed of a boro-silicate glass, provided with two or more pull-out preventive undercuts at the entrance end portion and exit end portion along a circumferential direction or adjacent two or more circumferential directions with holding a space therebetween. Also, outer diameter of a portion of the flanged cap, other than its flange, is preferred to be not greater than that of the glass barrel.

In the glass cartridge for the injection syringe of the present invention, the lure lock lid can be an assembly made by laminating an inner lure lock lid and an outer lure lock lid. The inner lure lock lid in contact with the gasket is preferably formed of a polyolefin resin. The outer lure lock lid in contact with the lid holder is preferably formed of a resin selected from a thermoplastic polyester resin, a polyamide resin and a polysulfon resin; mixed resins of two or more of these; and mixed resins thereof with ethylene-vinyl alcohol copolymer.

In the glass cartridge for the injection syringe of the present invention, when the lure lock lid is the assembly made by combining an inner lure lock lid and an outer lure lock lid, the inner lure lock lid may comprise an outer cylindrical part having a collar on one end, which is disposed in the exit end portion of the glass barrel. A conical bottom part is disposed on the other end of the barrel part and an inner cylinder starting from the vicinity of the central axis of the bottom part in a long and narrow tubular form. Also, provided is an annular engaging projection line surrounding the base part of the inner cylinder, while the outer lure lock lid may be made to have a form roughly similar to that of the inner lure lock lid and be provided with an inner cylinder having an inner diameter large enough to be inserted into the inner cylinder of the inner lure lock lid and an annular engaging projection on the entrance end of its inner cylinder which gets engaged with the annular engaging projection of the inner lure lock lid.

Further, on the glass cartridge for the injection syringe of the invention, both the lid holder and the flanged cap are preferably made of a polycarbonate resin.

BRIEF DESCRIPTION OF THE DRAWINGS

FIG. 1A shows a side view of a preferred embodiment of the glass cartridge for the injection syringe according to the present invention.

FIG. 1B shows a sectional view of the glass cartridge of the embodiment illustrated in FIG. 1A.

DETAILED DESCRIPTION OF THE INVENTION

Figure 2:
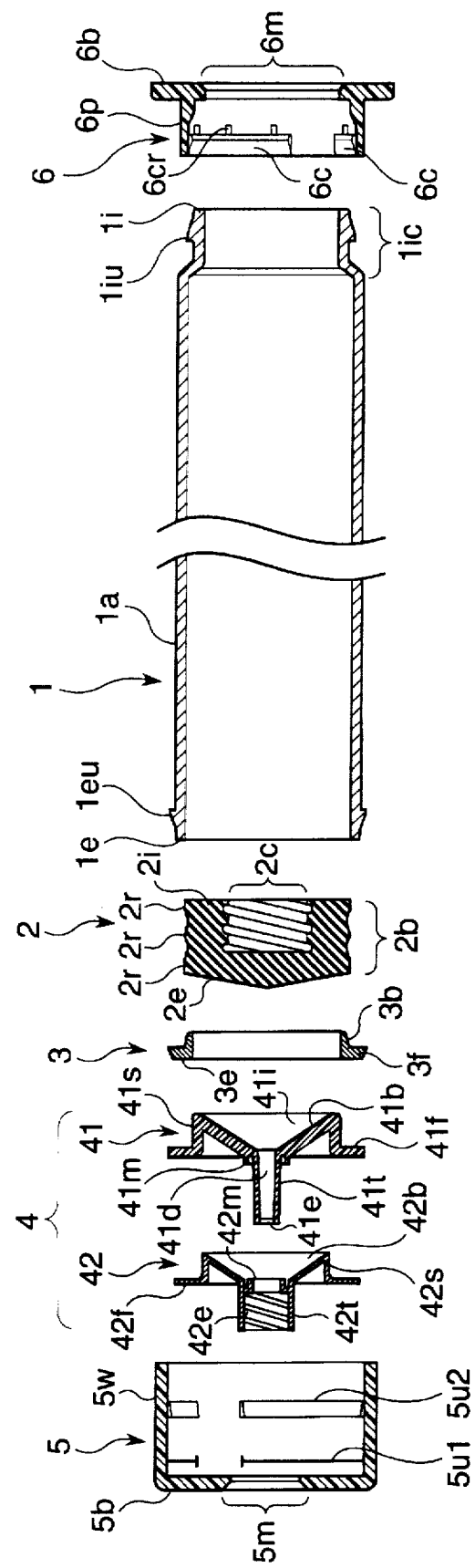
FIG. 2 shows an exploded sectional view of the glass cartridge of FIG. 1A.

Preferred embodiments of the glass cartridge for the injection syringe according to the present invention will be described in detail with reference to the accompanying drawings.

FIG. 1A shows a side view of a preferred embodiment of the glass cartridge for the injection syringe according to the present invention, and FIG. 1B shows a sectional view thereof. As shown in FIG. 1A, in the glass cartridge of the embodiment, starting from a lure lock plug a connector and a pipeline connected to a catheter can be attached to the tip of the exit end side while a plunger can be attached from the entrance end. As shown in FIG. 1B, both the lure lock plug and the plunger can be detached while other members are maintained in an attached condition.

FIG. 2 shows an exploded longitudinal sectional view of the glass cartridge for the injection syringe of the embodiment.

As shown in FIGS. 1A, 1B and 2, the glass cartridge (1) of the embodiment comprises a barrel made of a glass tube (1a), a stopper (2) serving also as a piston provided inside the glass barrel (1a) beforehand, a gasket (3) attached so as to be brought into contact with the exit end (1e) and an inner surface of the glass barrel (1a) in the vicinity of the exit end (1e), a lure lock lid (4) attached to the exit end (1e) portion of the glass barrel (1a) via the gasket (3), a lid holder (5) fitted onto the exit end (1e) portion of the glass barrel (1a) with holding the gasket (3) and the lure lock lid (4), and a flanged cap (6) provided on the entrance end (1i) portion of the glass barrel (1a).

FIG. 1B shows a plunger (7) to be fitted in a recess (2c) of the entrance side of the stopper (2) which also serves a piston.

<<GLASS BARREL 1a>>

The glass barrel (1a) is made of a transparent linear glass tube and serves as an injection syringe main body. The glass barrel is provided with a pull-out prevention type undercut (1eu) formed on the outer surface of the exit end (1e) portion. The entrance end (1i) portion which is a reduced diameter area (1ic) reduced in diameter and extending from a large diameter part including the entrance end (1i) portion through a step-down part, and another pull-out preventive type undercut (1iu) on the outer surface of the entrance end (1i) portion. The outer diameter of this entrance end portion (1i) is reduced so as to allow the outer diameter of the flanged cap (6) provided thereon to be below that of other areas of the barrel (1a).

<<STOPPER (2) SERVING ALSO AS PISTON>>

The stopper (2), serving also as the piston, comprises a head part (2e) having an obtuse apex angle extending toward an exit side and a body part (2b) roughly in a cylindrical form. The body part (2b) is provided with a recess part (2c) on an entrance side surface (2i). The diameter and depth of the recess part (2c) are large enough to house a head part (7h) of the plunger (7).

Three circumferential projection lines on ribs (2r) are provided on the outer periphery of the stopper (2). The projection lines referred to as rings and are brought into contact with the inner surface of the barrel (1a) to seal liquid being stuck to the inside of the glass cartridge (1). Thus, the lines (2r) are respectively independent of one another, the first is positioned on a skirt of the head part (2e), the second is positioned roughly on the middle of the body part (2b) and the third is positioned in the vicinity of the entrance end surface (2i) of the body part (2b).

<<GASKET (3)>>

The gasket(3) is disposed in the exit end (1e) portion of the glass barrel (1a) and comprises a main body (3f) of a ring form and an insertion part (3b) of a ring form projecting from an edge of an opening of the main body (3f) toward the glass barrel (1a). The main body (3f) of the gasket (3) is much thicker than the insertion part (3b). The main body (3f) is brought into contact with the exit end surface of the glass barrel (1a) while the insertion part (3b) is brought into contact with the inner surface adjacent the exit end (1e) of the glass barrel (1a) and tapers toward the inside slightly. The gasket (3) serves to form a tight seal between the exit end (1e) surface of the glass barrel (1a) and the lure lock lid (4) which is brought into contact with an interior surface of the gasket (3).

<<LURE LOCK LID (4)>>

The lure lock lid (4) is an assembly made by laminating an inner lure lock lid (41) and an outer lure lock lid (42). The inner lure lock lid (41) has a funnel-shaped bottom (41b) which makes the entrance side surface (41i) of the inner lure lock lid (41) have a recess roughly similar to the shape of the head part (2e) of the stopper (2) so as to receive it. On the axis of the bottom (41b), the peripheral edge of a liquid supplying hole (41d) is extended to form an inner cylinder (41t) having the exit opening (41e). Further, on the periphery of the funnel-shaped bottom (41b) a pleated tube part (41s: outer cylinder) folded toward the exit side and protruding roughly in parallel to the axis, and a flange part (41f) starting from the exit end of the pleated tube part (41s) are provided.

The exit side surface of the inner lure lock lid (41) has a shape having an apex angle formed similar to that of the entrance side surface. The shape of the exit side surface is also given by the conical bottom part (41b) having an obtuse angle, an outer cylinder (41s) steeply started from the end point of the bottom part (41b) and an inner cylinder (41t) starting from the center of the bottom within the inside of the outer cylinder (41s). The inner cylinder (41t) is made in a tapered and relatively thin cylindrical form. Further, an annular engaging projection (41m) surrounding the base part of the inner cylinder (41t) is provided.

On the other hand, the outer lure lock lid (42) is positioned on the outside of the inner lure lock lid (41), that is, on the same side of the lid holder (5) and is made in a form roughly similar to the inner lure lock lid (41).

That is, the outer lure lock lid (42) comprises a conical funnel-shaped bottom (42b) with an obtuse apex angle, of which an exit side (42e) surface is almost similar to the shape of the entrance side thereof and an inner cylinder (42t) steeply starting from the center of the bottom part (42b). On the other hand, on the periphery of a bottom part (42b) the pleated tube (outer cylinder) part (42s) is folded to the exit side and projected in parallel to the axis, and a flange part (42f) expands outwardly from the tip of the pleated tube part or outer cylinder (42s).

The diameter of the inner cylinder (42t) of the outer lure lock lid (42) is formed relatively large and the inner cylinder (41t) of the inner lure lock lid (41) is inserted thereinto. On the inner surface of the inner cylinder (42t) a means, for example, a male screw, for engaging with two slight projections (8b) installed symmetrically on the lower end of a lure lock plug (8a) is provided. Further, an annular engaging projection (42m) with a smaller diameter is provided on the inner base part of the inner cylinder (42t) of the outer lure lock lid (42) and engages with the engaging annular projection (41m).

The back side of the flange part (42f) of the outer lure lock lid (42) is brought into contact with the surface of the flange part (41f) of the inner lure lock lid (41). Also, the outer lure lock lid (42) is housed in a space between the back side of the funnel-shaped part (41b) and the inner wall of the pleated tube part or outer cylinder (41s) of the inner lure lock lid (41).

It should be noted that the bottom part (42b) and the pleated tube part or outer (42s) of the outer lure lock lid (42) are housed in a space between the back side of the funnel-form part (41b) of the inner lure lock lid (41) and the inner wall of the pleated tube part (41s) folded from its periphery to the axial direction. Also, the flange part (42f) of the outer lure lock lid (42) is made smaller in the outer diameter than the flange part (41f) of the inner lure lock lid (41).

By such combination of the inner lure lock lid (41) and the outer lure lock lid (42), the inner lure lock lid (41) made from a material as polyolefin (PO) comes into contact with a pharmaceutical liquid and leakage of the pharmaceutical liquid passed through and between the gasket (3) and the inner lure lock lid (41) can be stopped by an outer lure lock lid (42) made from polybutylene terephthalate (PBT).

<<LID HOLDER (5)>>

The lid holder (5) is a cylinder with a bottom, and basically comprises a bottom plate (5b) and a cylindrical side wall (5w). The bottom plate (5b) is provided with an opening (5m) having a diameter large enough to allow the inner cylinder (42t) of the outer lure lock lid (42) project from the center of the bottom plate (5b). The lid holder (5) serves to hold and fix the lure lock lid (4) and the gasket (3) in a state in which they are tightly pressed against the exit end (1e) of the glass barrel (1a).

The lid holder (5) is provided with an undercut (5ul) on the bottom plate side inner surface of side wall (5w) in order to restrain the lure lock lid (4) in the state that the inner cylinder (42t) of the outer lure lock lid (42) projects from the opening (5m) and that the flange part (42f) of the outer lure lock lid (42) is in contact with an inner surface of the bottom plate (5b) of the lid holder (5).

The lid holder (5) is further provided with another undercut (5u2) on the entrance side inner surface of side wall (5w) in order to fix both the flange parts (41f), (42f) of the lure lock lid (4) and the gasket (3) on the glass barrel (1a) with pressure. The section of this undercut (5u2) is roughly saw blade-shaped (unequal-sided projecting part), disposed for being engaged with the undercut (1eu) provided on the outer surface of the exit end (1e) portion of the glass barrel (1a), which allows to the lid holder (5) to be attached without any resistance and will prevent its detachment.

Further, the sectional form of an undercut (5u1) positioned on the bottom side is also roughly saw blade-shaped, and serves to prevent further advance of the undercut (1eu). Thus, it is preferred that its sectional triangular shape must be one having relatively equal sides and projects rather high.

<<FLANGED CAP (6)>>

The flanged cap (6) is attached on the entrance end (1i) portion of the glass barrel (1a), and includes a flat flange (6b) and a cylindrical tubular part (6p) starting from a face of the flange (6b) opposed to the entrance end (1i) of the glass barrel (1a). An opening (6m) is provided on the central axis of the flange part (6b). The cylindrical tubular part (6p) has an outer diameter which is less than or equal to the outer diameter of the glass barrel—has been added after "(6b).".

An undercut (6c) is provided on a predetermined position of the inner surface of the tubular part (6p) and is engaged with the undercut (1iu) provided on the outer surface of the entrance end (1i) portion of the glass barrel (1a). The undercut (6c) is normally divided into two or more portions, in the case of the present embodiment it is divided into three or four portions. The amount of a space between two adjacent undercuts (6c) is determined so as to make the undercuts (1iu) of the glass barrel (1a) pass between the undercuts (6c) so as to be engaged therewith.

The undercut (1iu) may be also divided having the same number and the same sized space as the undercut (6c). However, the undercut (1iu) and/or the undercut (6c) may be successively and integrally formed. The shape of the undercut (6c) may be selected depending on the characteristics of a material of the flanged cap (6).

The sections of both undercuts are made in a saw blade-shape and are designed such that they can prevent detachment of the flanged cap (6) but allow the cap (6) to be attached without any resistance. Further, the undercut (6c) is provided with a number of small ribs (6cr) projecting toward the inside from the inner surface of the flanged cap (6). A number of these small ribs are slightly deformed by the advance of the undercut (1iu), and serve to prevent rotation of the glass barrel (1a) by a slight pressure generated by deformation and to limit its play.

The number of the small ribs (6cr) is preferably increased with the increase of the outer diameter of the entrance area (1i) portion of the glass barrel (1a). In the case of the glass cartridge holding pharmaceutical liquid having a capacity of 50–300 ml, the number must be normally from 10 to 16, preferably over 12, and they may be set at roughly equal intervals. However, in the case where the undercuts (6c) are two or more in number, the distance among small ribs, means the distance among the small ribs existing on the same undercut (6c) but does not include the spacing between the undercuts (6c).

The diameter of the opening (6m) is made roughly similar to the inner diameter of the entrance end (1i) of the glass barrel (1a). However, the inner diameter must be set at a value sufficient at least to allow the plunger (7) to be inserted therethrough.

<<ADDITIONAL MEMBERS>>

Additional members shown in FIGS. 1A and 1B are not component parts of the glass cartridge (1) for the injection syringe prefilled with pharmaceutical liquid according to the present embodiment. However, they are members to be attached when the glass cartridge is put to actual use. These members will be described in brief.

<<PLUNGER (7)>>

FIG. 1A shows a glass cartridge (1) attached with the plunger (7) for use. The function of the plunger is to advance the stopper (2) into the glass cartridge (1) for the injection syringe prefilled with pharmaceutical liquid (1).

As shown in FIG. 1B, the plunger (7) includes a roughly cylindrical main part (7g) and a head part (7h) comprised of a short cylindrical part projecting from the tip of the main part. The plunger usually has a roughly bar-shaped handle part (not shown) extending from the terminal end of the main part to the outside. The dimension and size of the head part (7h) is to correspond to a recess part (2c) provided in the bottom of the stopper (2). The plunger (7) functions to advance the stopper (2) into the glass barrel (1a) when the head part (7h) is fitted into the recess (2c) of the stopper (2).

A plunger of another embodiment (not shown) is used in the state that a plunger socket is integrally attached to its tip area. The form of the plunger in this case is roughly bar-shaped, and a male screw is provided on its tip area as a means for engaging with a plunger socket which will be described below.

<<PLUNGER SOCKET (not shown)>>

A plunger socket is planned to be made separately from the above referred plunger of another embodiment, but to be used by combining with it and made one unit.

In this case, the tip of the plunger is provided with a male screw for connecting the socket. The socket mainly constructs an insertion portion into the stopper (2) and may have a flange in order to define its position integrally. Further, the socket has a female screw to be connected with the plunger main body.

<<LURE LOCK PLUG (8)>>

As shown in FIGS. 1A and 1B, the lure lock plug (8a) is an opened conical tip part positioned on the lure lock lid side of a connector (or adapter) (8) connected to a catheter to be penetrated into an injection position. The lure lock plug (8a) is provided with two slight projections (8b) disposed symmetrically on a longitudinal axis on its tip. These projections (8b) are engaged with an engaging means, for example, a female screw provided on the inner cylinder (42t) of the outer lure lock lid (42) to fix the connector (8).

<<MATERIAL FOR EACH PART>>

Materials for respective component parts of the glass cartridge for the injection syringe filled with pharmaceutical liquid according to the present invention will be described.

The glass barrel (1) is made of a hard glass, preferably a heat resistant glass, more preferably a boro-silicate glass. Needless to say, it is most preferable that it is made of quartz in the view point of resistance to chemicals. Though boro-silicate glass can be vulnerable to strong alkali, as strong alkaline chemicals are not usually used for medical purposes, no actual problem will occur. Further, it is much stronger than a hard glass in terms of resistance to thermal shock, etc.

The stopper (2) and the gasket (3) attached to the exit end (1e) thereof are equally formed of soft materials, normally rubbers, and in particular a butyl rubber ("IIR", that is, isobutylene-isoprene copolymer rubber) used. These soft materials should have an excellent gas barrier characteristic in addition to resistance to heat of 121° C.×20 min (reduction in heat resistance, deformation by heat, etc., will not occur) which is a requirement for steam sterilization by pressure.

As for an assembly for forming the lure lock lid (4) to be fitted into the exit end (1e) of the glass barrel, the inner lure lock lid (41) and the outer lure lock lid (42) is made of flexible resins. In addition, the inner lure lock lid (41) is preferably formed of biochemically inert materials, such as a polyolefin (PO) resin including polypropylene resin and the outer lure lock lid (42) is preferably formed of materials having excellent heat resistance for preventing deformation and a good mechanical characteristic. For example, the materials for the outer lure lock lid (42) are selected from the group consisting of polybutylene terephthalate (PBT), polyamide (NY), polysulfon resins, mixed resins of two or more of these, and mixed resins of one or more of these with ethylene-vinyl alcohol copolymer (EVOH).

The lid holder (5) is lastly provided on the exit end (1e) of the glass barrel (1) so as to fix the lure lock lid (4) and the gasket (3) on the exit end (1e). Therefore, materials for the lid holder (5) are selected in view of a necessary mechanical characteristic, heat resistance and moldability rather than its interaction with contained chemicals. For example, a polycarbonate resin is often used, which is extremely excellent in view of exact dimensions of such as undercuts, etc., made by transferring from the shape of the metallic mold and the impact-proof properties.

Further, the flanged cap (6) is provided on the entrance end (1i) of the glass barrel (1a) and its flange (6b) serves as a fingerplate for pushing the plunger (7) into the glass barrel (1a) and besides, it is important that it is suited to the loading device of the Auto-Injector normally on later use. Thus, a material for the flanged cap (6) preferably has the same characteristic as the material for lid holder (5), and, therefore, a polycarbonate resin is commonly used.

The plunger (7) and the plunger socket are preferably all made of polyolefin resin, such as polypropylene resins. This selection has been made to be on the safe side, even though they are not brought into direct contact with the pharmaceutical liquid. Of polypropylene resins, the one having resistance to pressurized steam sterilization is desired to be selected.

At the glass cartridge for the injection syringe prefilled with pharmaceutical liquid of the embodiment, the following effects are realized synergistically;

(a.) Engagements are made respectively between the pull-out preventive type undercuts (1iu) and (1eu) provided on the peripheries of the entrance and exit end (1i), (1e) portions of the glass barrel (1a) and between the undercuts (6c) or (5u) projectingly and/or concavingly provided on the inner walls of the flanged cap (6) and the lid holder (5), and thereby liquid leakage and pull-out will be prevented when they are exposed to pressure steam sterilization (121° C.×20 min).

(b.) The lure lock lid (4) is assembled by combining the inner and outer lock lids (41), (42) and the former is made of a polyolefin resin, such as a polypropylene resin, while the latter is made of a resin material selected from high-melting point thermoplastic polyester such as PBT, thermoplastic polyamide such as 6-nylon, polysulfon resins, mixed resins of two or more of these, and the mixed resins of one or more of these with ethylene-vinyl alcohol copolymer resin (EVOH), and thus even when the resins lose their heat resistance due to pressurized steam sterilization (121° C.×20 min) and/or they are exposed to increase of inner pressure generated by e.g. expansion, evaporation, volatilization, etc. of pharmaceutical liquid, the condition that liquid leakage and pulling-out are prevented will be further strengthened.

(c.) The lid holder (5) and the flanged cap (6) are both made of a heat resistant thermoplastic resin, in particular a polycarbonate resin, and thus when they are exposed to steam sterilization by pressure (121° C.×20 min), liquid leakage and pulling-out will be effectively prevented. It practically suffices if the flange (6) is made of a polypropylene resin.

(d.) Even when it is brought into contact with high-temperature pharmaceutical liquid during pressurized steam sterilization, alkaline metallic ions will not be eluted, and thus quality of pharmaceutical liquid will not be deteriorated.

EFFECT OF THE INVENTION

The following effects will be realized by using the glass cartridge for the injection syringe prefilled with pharmaceutical liquid according to the present invention:

(1) The cartridge made of general purpose, industrial material is not subject to liquid leakage and pull-out even when it is exposed to pressure steam sterilization (121° C.×20 min).

(2) Even when it is brought into contact with high-temperature pharmaceutical liquid during pressurized steam sterilization, alkaline metallic ions will not be eluted, and thus quality of the pharmaceutical liquid will not deteriorate.

(3) It will be made possible to securely contain, transport and store a relatively large volume of pharmaceutical liquid ranging from 50 to 300 ml, easily load it into the injection device as it is, and thereby to use for injecting pharmaceutical liquid.

(4) It will be made possible to use in the same manner as described above for medical use as X-ray Contrast Media, or the like difficult to be contained in the injection syringes.

(5) It will be made easy to break it down and divide it into combustibles and incombustibles prior to disposition after use.

Hereinafter, the effects of the invention are concretely described in the following experiment.

EXPERIMENT

Glass syringes of the prior art each of which had integrally formed ends, and syringes according to the present embodiment as shown in FIG. 1 having the same capacity were manufactured from various boro-silicate glasses. Into these syringes introduced was physiological saline (pH. 5.7) and they were subjected to pressurized steam sterilization (121° C.×1 h). Thereafter, the pH of the saline in each of syringes was measured. The results are shown in Table 1.

As shown in Table 1, in each of syringes according to the embodiment of FIG. 1A, the pH was hardly changed. From the results, it is understood that alkali components were difficult to elute into the saline.

TABLE 1

| Variety of generally sold boro-silicate glasses | | Elution index (pH) of alkaline components from the inner wall of the glass injection syringe | |
|---|---|---|---|
| | | | Products with both ends (both end |
| Product name | Line expansion co-efficient (× 10⁻⁷) | Sample No. | Products of this embodiments | resin) integrally formed (both ends made of glass) |
| SIRIX | 49 | 1 | 5.8 | 6.3 |
| | | 2 | 5.7 | 6.2 |
| | | 3 | 5.8 | 6.5 |
| N-51-A | 50 | 1 | 5.8 | 6.4 |
| | | 2 | 5.8 | 6.5 |
| | | 3 | 5.9 | 6.7 |
| BS | 52 | 1 | 5.9 | 6.8 |
| | | 2 | 5.8 | 6.7 |
| | | 3 | 5.9 | 6.9 |

Solvent for elution: Physiological salt solution (pH 5.7)
Condition for sterilization (elution) by steaming under pressure: 121° C. × 1 h

What is claimed is:

1. A glass cartridge for an injection syringe prefilled with pharmaceutical liquid, said cartridge comprising:

a barrel formed of a heat resistant glass, said barrel being provided with a first undercut on an outer surface of an exit end portion of said barrel, and a second undercut on an outer surface of an entrance end portion of said barrel;

a lid holder disposed on said exit end portion of said barrel in engagement with said first undercut, said lid holder being formed of a flexible material;

a gasket disposed between said lid holder and an exit end surface of said barrel, said gasket being formed of a soft material;

11 a lure lock lid provided between said gasket and said lid holder, said lure lock lid being formed of multiple pieces of flexible material;

a stopper disposed in said barrel, said stopper also serving as a piston; and a flanged cap disposed on said entrance end portion of said barrel in engagement with said second undercut, said flanged cap being formed of a flexible material and including a flange portion, having a central axis, and a hollow cylindrical portion extending axially from a side face of said flange portion, wherein said entrance end portion of said barrel includes a stepped portion forming a reduced diameter portion, and said flanged cap is received on said reduced diameter portion such that an outer peripheral surface of said cylindrical portion does not project radially beyond said outer peripheral surface of said barrel at any location of said barrel other than said flange portion.

2. The glass cartridge as claimed in claim 1, wherein said barrel is a linear transparent glass tube formed of a borosilicate glass.

3. The glass cartridge as claimed in claim 2, wherein said cylindrical portion of said flanged cap includes a plurality of discrete pull-out prevention projections aligned in a plane substantially perpendicular to the central axis of said flange portion, and said projections are spaced circumferentially so as to permit said second undercut to pass upon application of said flanged cap on said entrance end of said barrel.

4. The glass cartridge as claimed in claim 3, wherein an outer diameter of said cylindrical portion is less than or equal to the outer diameter of said barrel.

5. The glass cartridge as claimed in claim 4, wherein said lid holder and said flanged cap are formed of polycarbonate resins.

6. The glass cartridge as claimed in claim 1, wherein said lid holder and said flanged cap are formed of polycarbonate resins.

7. The glass cartridge as claimed in claim 1, wherein the diameter of said barrel is constant along said barrel except at said reduced diameter portion so as to avoid inducing thermal stresses therein.

8. A glass cartridge for an injection syringe prefilled with pharmaceutical liquid, said cartridge comprising:

a barrel formed of a heat resistant glass, said barrel being provided with a first undercut on an outer surface of an exit end portion of said barrel, and a second undercut on an outer surface of an entrance end portion of said barrel;

a lid holder disposed on said exit end portion of said barrel in engagement with said first undercut, said lid holder being formed of a flexible material;

a gasket disposed between said lid holder and an exit end surface of said barrel, said gasket being formed of a soft material;

a lure lock lid provided between said gasket and said lid holder, said lure lock lid being formed of a flexible material;

a stopper disposed in said barrel, said stopper also serving as a piston; and a flanged cap disposed on said entrance end portion of said barrel in engagement with said second undercut, said flanged cap being formed of a flexible material, wherein said lure lock lid comprises an inner lure lock lid and an outer lure lock lid laminated to said inner lure

12 lock lid, said inner lure lock lid contacts said gasket and is formed of polyolefin resin, said outer lure lock lid contacts said lid holder and is formed of a resin selected from a thermoplastic polyester resin, a polyamide resin and a polysulfon resin, mixed resins of two or more said resins, and mixed resins thereof with an ethylene-vinyl alcohol copolymer.

9. The glass cartridge as claimed in claim 8, wherein said barrel is a linear transparent glass tube formed of a borosilicate glass.

10. The glass cartridge as claimed in claim 9, wherein said flanged cap includes a flange portion, having a central axis, and a hollow cylindrical portion extending axially from a face of said flange portion.

said cylindrical portion includes a plurality of discrete pull-out prevention projections aligned in a plane substantially perpendicular to the central axis of said flange portion, and said projections are spaced circumferentially so as to permit said second undercut to pass upon application of said flanged cap on said entrance end of said barrel.

11. The glass cartridge as claimed in claim 10, wherein an outer diameter of said cylindrical portion is less than or equal to the outer diameter of said barrel.

12. The glass cartridge as claimed in claim 11, wherein said lid holder and said flanged cap are formed of polycarbonate resins.

13. The glass cartridge as claimed in claim 8, wherein said lid holder and said flanged cap are formed of polycarbonate resins.

14. The glass cartridge as claimed in claim 8, wherein said barrel is of a constant diameter at said exit end portion so as to avoid inducing thermal stresses therein.

15. A glass cartridge for an injection syringe prefilled with pharmaceutical liquid, said cartridge comprising:

a barrel formed of a heat resistant glass, said barrel being provided with a first undercut on an outer surface of an exit end portion of said barrel, and a second undercut on an outer surface of an entrance end portion of said barrel;

a lid holder disposed on said exit end portion of said barrel in engagement with said first undercut, said lid holder being formed of a flexible material;

a gasket disposed between said lid holder and an exit end surface of said barrel, said gasket being formed of a soft material;

a lure lock lid provided between said gasket and said lid holder, said lure lock lid being formed of a flexible material and comprising an inner lure lock lid and an outer lure lock lid, said inner lure lock lid including an outer cylindrical part disposed in said exit end portion of said barrel and having a collar at one end thereof, a conical bottom portion extending from the other end of said outer cylindrical part, an inner cylinder extending along a central axis of said bottom portion from a converging end of said conical bottom portion so as to define a long and narrow tubular form, and an annular engaging projection surrounding a base portion of said inner cylinder, said outer lure lock lid having a form similar to that of said inner lure lock lid and being provided with an inner cylinder having an inner diameter of a size such that said inner cylinder of said inner lure lock lid can be inserted into said inner cylinder of said outer lure lock lid, and an annular projection projecting from an inner surface of said inner cylinder of said outer lure lock lid and engaged with said annular engaging projection of said inner lure lock lid;

a stopper disposed in said barrel, said stopper also serving as a piston; and a flanged cap disposed on said entrance end portion of said barrel in engagement with said second undercut, said flanged cap being formed of a flexible material.

16. The glass cartridge as claimed in claim 15, wherein said barrel is a linear transparent glass tube formed of a boro-silicate glass.

17. The glass cartridge as claimed in claim 16, wherein said flanged cap includes a flange portion, having a central axis, and a hollow cylindrical portion extending axially from a face of said flange portion, said cylindrical portion includes a plurality of discrete pull-out prevention projections aligned in a plane substantially perpendicular to the central axis of said flange portion, and said projections are spaced circumferentially so as to permit said second undercut to pass upon application of said flanged cap on said entrance end of said barrel.

18. The glass cartridge as claimed in claim 17, wherein an outer diameter of said cylindrical portion is less than or equal to the outer diameter of said barrel.

19. The glass cartridge as claimed in claim 18, wherein said lid holder and said flanged cap are formed of polycarbonate resins.

20. The glass cartridge as claimed in claim 5, wherein said lid holder and said flanged cap are formed of polycarbonate resins.

21. The glass cartridge as claimed in claim 15, wherein said barrel is of a constant diameter at said exit end portion so as to avoid inducing thermal stresses therein.

* * * * *